United States Patent [19]
Zuo et al.

[11] Patent Number: 5,753,207
[45] Date of Patent: May 19, 1998

[54] USE OF PARAMAGNETIC COMPOUNDS TO MEASURE TEMPERATURE AND PH IN VIVO

[75] Inventors: Chun S. Zuo, Lexington; Melvin E. Clouse, Brookline, both of Mass.

[73] Assignee: Beth Israel Deaconess Medical Center, Inc., Boston, Mass.

[21] Appl. No.: 699,496

[22] Filed: Aug. 19, 1996

Related U.S. Application Data

[60] Provisional application No. 60/002,539, Aug. 21, 1995.
[51] Int. Cl.$^6$ .................................................. A61B 5/055
[52] U.S. Cl. ............... 424/9.36; 424/9.363; 514/184; 514/492; 514/502; 514/836; 128/653.4; 128/654; 436/173
[58] Field of Search ............... 424/9.36, 9.363; 128/653.4; 436/173; 514/184, 836, 492, 502

[56] References Cited

U.S. PATENT DOCUMENTS

| | | | |
|---|---|---|---|
| 4,558,279 | 12/1985 | Ackerman et al. | 324/315 |
| 5,263,482 | 11/1993 | Leunbach | 128/653.2 |
| 5,397,562 | 3/1995 | Mason et al. | 424/9 |
| 5,468,467 | 11/1995 | Tweedle et al. | 424/9.361 |
| 5,512,268 | 4/1996 | Grinstaff et al. | 424/9.322 |
| 5,536,491 | 7/1996 | Asai et al. | 424/9.363 |
| 5,580,990 | 12/1996 | van den Berg et al. | 549/212 |

OTHER PUBLICATIONS

Zuo et al., *Proceedings RSNA*, 81st Annual Meeting; p. 423 (1995).

Aime et al., "A New Ytterbium Chelate as Contrast Agent in Chemical Shift Imaging and Temperature Sensitive Probe for MR Spectroscopy" *Magn. Resons. Med.* 35, 648–651 (1996).

Alsaadi et al., "Hydration of Complexone † Complexes of LanthanideCations", *J.C.S. Dalton* 271, 2151–2154 (1980).

Anderson et al., "Dynamic NMR measurement of volume regulatory changes in Amphiuma RBC Na$^+$ content" *Am. J. Physiol.*, vol. 254, pp. 466–474 (1988).

Bansal et al., "In Vivo Na–23 MR Imaging and Spectroscopy of Rat Brain during TMDOTP$^{5-}$ Infusion[1]" *J. Magn. Reson. Imag.* 2,385–391 (1992).

Bansal et al., "Thulium 1,4,7,10-Tetraazacyclododecane–1,4,7,10-tetrakis (methylene phosphonate) as a $^{23}$Na Shift Reagent for the in Vivo Rat Liver" *Biochemistry* 32, 5638–5643 (1993).

Bleaney B., "Nuclear Magnetic Resonance Shifts in Solution Due to Lanthanide Ions" *J. Magn. Reson.* 8, 91–100 (1972).

Bloembergen and Morgan, "Proton Relaxation Times in Paramagnetic Solutions. Effects of Electron Spin Relaxation" *J. Chem. Phys.* 34, 841 (1961).

Bornais and Brownstein, "A Low–Temperature Thermometer for H, F, and C" *J. Magn. Reson.* 29, 207–211 (1978).

Boulanger et al., "Monitoring of the Effects of Dysprosium Shift Reagents on Cell Suspensions" *NMR Biomed,.* vol. 5(1), pp. 1–10 (1992).

Brasch et al., "Work in Progress: Methods of Contrast Enhancement for NMR Imaging and Potential Applications" *Radiology,* vol. 147, pp. 781–788 (1983).

Bryden and Reilley, "Multinuclear Nuclear Magnetic Resonance Study of Three Aqueous Lanthanide Shift Reagents: Complexes with EDTA and Axially Symmetric Macrocyclic Polyamino Polyacetate Ligands" *Anal. Chem.* 53, 1418–1425 (1981).

Buster et al., "Tm (DOTP)$^{5-}$: A $^{23}$Na$^+$ Shift Agent for Perfused Rat Hearts" *Magn. Reson. Med.* 15, 25–32 (1990).

Butwell et al., "Influence of Cardiac Pacing on Intracellular Sodium in the Isolated Perfused Rat Heart" *Invest. Radiol.* 26, 1079–1082 (1991).

Cacciafesta et al., "$^{23}$Na–NMR study of cation cotransport in human red blood cells" *Am. J. Physiol.* vol. 262, pp. 1292–1296 (1992).

De Poorter et al., "Non–Invasive In–Vivo Thermometry with the Proton Resonance Frequence Method: Qualitative Results in Human Muscle" *Proc., SMRM,* 12th Annual Meeting, New York, p. 738 (1993).

De Poorter et al., "The Proton–Resonance–Frequency–Shift Method Compared with Molecular Diffusion for Quantitative Measurement of Two–Dimensional Time–Dependent Temperature Distribution in a Phantom" *J. Magn. Reson.* B103, 234–241 (1994).

Drago et al., "Theory of Isotropic Shifts in the NMR of Paramagnetic Materials" *J. Chem. Educ.* 51, 371–376, 464–467 (1974).

Frenzel et al., "Noninvasive Temperature Measurement in Vivo Using a Temperature–Sensitive Lanthanide Complex and H Magnetic Resonance Spectroscopy" *Magn. Reson. Med.* 35, 364–369 (1996).

Frenzel et al., "Non–Invasive In Vivo Temperature Measurement Using a Lanthanide Complex and Proton MR–Spectroscopy" Proceedings of the SMR, 4th Annual Meeting, Nice (Aug., 1995).

(List continued on next page.)

*Primary Examiner*—Gary E. Hollinden
*Attorney, Agent, or Firm*—Lahive & Cockfield, LLP

[57] ABSTRACT

A method for measuring temperature and/or pH in vivo using paramagnetic compounds, e.g., lanthanide complexes, in conjunction with NMR has been developed. The chemical shift of the nuclear spin in these complexes can then be correlated to temperature. This non-invasive temperature measurement method is particularly useful in monitoring temperature of cancerous tissue during hyperthermic treatment to destroy the cancerous tissue or tumor.

9 Claims, 7 Drawing Sheets

OTHER PUBLICATIONS

Friebe et al., "Fesibility Evaluation of Several MR Thermometry Methods for Hyperthermia Applications for Low–Field MR Imaging" Proc., 81th Annual Meeting RSNA, Chicago, p. 424 (1995).

Geraldes et al., "The Solution Structure of $Ln(DOTP)^{5-}$ Complexes. A Comparison of Lanthanide–Induced Paramagnetic Shifts with the MMX Energy–Minimized Structure" *J. Magn. Reson.* 97, 290–304 (1992).

Levy et al., "A Sensitive NMR Thermometer for Multinuclei FT NMR" *J. Magn. Reson.* 37, 353–356 (1980).

Shukla et al., "A Comparison of Three Commercial Perfluorocarbon Emulsions as High–Field $^{19}F$ NMR Probes of Oxygen Tension and Temperature" *J. Magn. Reson.* B106, 131–141 (1995).

Webb et al., "Cobalt–59 functional agents for localized in–vivo temperature measurements" Proc., SMRM, 12th Annual Meeting, New York, p. 245, 1993.

Young et al., "Modeling of Tissue Response to Temperature as Depleted In Vivo with Water–Peak Phase–Shift Method" Proc., RSNA, 81th Annual Meeting, Chicago, p. 423 1995.

USE OF PARAMAGNETIC COMPOUNDS TO MEASURE TEMPERATURE AND PH IN VIVO

This invention was made, in part, with government support from the National Institute of Health (NIH grant P41-RR02584). Accordingly, the government retains certain rights in the invention.

This application claims the benefit of a previously filed Provisional Application No. 60/002,539, filed Aug. 21, 1995, which is hereby incorporated by reference.

BACKGROUND OF THE INVENTION

A problem of accurately and non-invasively measuring tissue temperature in vivo exists today, especially in deep seated tissues such as liver or other abdominal regions which are far away from the skin. Therefore, a need exists to develop a novel non-invasive method for sensitive temperature measurements in biological tissues. Magnetic resonance imaging and spectroscopy are promising technologies for performing non-invasive temperature measurements in vivo. Chemical shifts of nuclear spin under applied magnetic fields have been used to measure temperature in a number of circumstances, including attempts to measure tissue temperature in a non-invasive manner. A major obstacle in the use of chemical shifts to measure tissue temperature is insufficient accuracy at clinically used magnetic field strengths. The typical temperature dependence of the chemical shift for currently used thermometric materials such as protons in water or fluorocarbons is less than $1 \times 10^{-2}$ ppm/°C. for $^1$H, and $1 \times 10^{-2}$ ppm/°C. for $^{19}$F (J. Bornais et al., *J Magn. Reson.* (1978) vol. 29, p. 207). For a 1° C. temperature change, this corresponds to $\leq 0.7$ Hz/°C. at 1.5 Tesla, the field strength commonly used clinically (Young et al., "Proc., RSNA, 81th Annual Meeting, Chicago, 1995," p. 423; De Poorter et al., "Proc., SMRM, 12th Annual Meeting, New York, 1993," p. 738; Friebe et al., "Proc., 81th Annual Meeting RSNA, Chicago, 1995," p. 424). This weak temperature dependence, which results in poor temperature resolution (>2° C.), places stringent requirements on the static field homogeneity; which is often difficult to achieve under clinical conditions. These stringent requirements limit the clinical applications of magnetic resonance imaging for temperature measurements. One of such applications is hyperthermia.

Studies carried out over the past decade have established that hyperthermia in combination with radiation therapy or chemotherapy is an effective treatment for cancerous tissue. During hyperthermia, temperatures lower than 42° C. will not kill tumor cells and may in fact induce thermal resistance. On the other hand, temperature that are too high will damage much of the surrounding tissue. The difference between the destructive temperature necessary for tumor ablation and well tolerated temperatures in healthy tissue is only 1°–2° C., so a thermal resolution of about ±0.5° C. is required during hyperthermia. The weak temperature dependence of the magnetic resonance/water-proton materials used to date prohibit this technique from being used for temperature resolution at clinically used field strengths.

At present, the tissue temperature during a hyperthermia procedure is monitored using temperature sensors which are introduced at specific points in the body near the tissue undergoing treatment. The use of this technique has several shortcomings; it is invasive, the patient has to endure considerable stress, and it may not accurately measure temperature in the full volume of the tumor. As a temperature increase of about 5°–10° C. is needed to kill tumor cells, an inaccurate temperature reading in some part of a tumor could lead to premature termination of the hyperthermia prior to elimination of all of the tumor cells, or excess heating of surrounding, healthy tissue.

Thus, a need still exists for compounds with a larger chemical shift temperature dependence that could be more useful for in vivo or in vitro temperature measurements.

In general, the chemical shift of a nuclear spin in a paramagnetic compound ($\sigma$) is a sum of a paramagnetic term ($\sigma_e$) and a diamagnetic term ($\sigma_d$):

$$\sigma = \sigma_e + \sigma_d$$

Paramagnetic electrons contribute primarily to $\sigma_e$ while nearby nuclear spins form the major contribution to $\sigma_d$. It can be shown that $\sigma_e$ is a function of temperature T and, often, of pH as well, depending on the structure of the complex. Although $\sigma_e$ has a much larger temperature dependence than $\sigma_d$, thus far the use of the chemical shift for temperature measurement has only been explored for the diamagnetic part of the chemical shift ($\sigma_d$).

Accordingly, it is the object of the present invention is to provide a method of measuring temperature in vivo non-invasively with better accuracy.

Another object of the invention is to provide a method of accurately measuring temperature during hyperthermia treatment.

These and other objects and features of the invention will be apparent from the Description, the Drawing, and the Claims.

SUMMARY OF THE INVENTION

It has been discovered that certain paramagnetic compounds, such as lanthanide complexes, can be used to measure temperature in biological tissue with greatly improved accuracy. These compounds appear to exhibit large changes in a chemical shift in response to a temperature change. It is theorized that the paramagnetic part of the chemical shift of nuclear spins is involved in this temperature dependence. Thus, the present invention pertains to methods for measuring temperature change in a biological tissue by administering a paramagnetic compound to the biological tissue and subjecting the biological tissue to a varying magnetic field such as is used in magnetic resonance imaging.

In order to determine a change in temperature ($\Delta T$), a paramagnetic compound is administered to the biological tissue and the biological tissue is subjected to a magnetic field. The temperature change from $T_0$ to $T_1$ ($dT = T_1 - T_0$) is determined using the following bivariable linear equations:

$$\Delta \delta^H = C_T^H dT + C_{pH}^H dpH$$

$$\Delta \delta^P = C_T^P dT + C_{pH}^P dpH$$

wherein $\Delta \delta = \delta_1 - \delta_0$ (for both $^1$H and $^{31}$P), dpH is the pH change in the tissue caused by the temperature change. $C_T^H$, $C_T^P$, $C_{pH}^H$, and $C_{pH}^P$ temperature dependencies and pH dependencies of the chemical shifts respectively, are determined empirically. The solution (temperature and pH changes) can be expressed as $$dT = \Delta_T / \Delta, \quad dpH = \Delta_{pH} / \Delta,$$

where $\Delta_T = \Delta \delta^H \cdot C_{pH}^P - \Delta \delta^P \cdot C_{pH}^H$, $\Delta_{pH} = \Delta \delta^H \cdot C_T^P - \Delta \delta^P \cdot C_T^H$, and $\Delta = C_T^H \cdot C_{pH}^P - C_T^P \cdot C_{pH}^H$. In general, H and P can be any two non-magnetic equivalent nuclear spins.

If the pH remains unchanged (dpH=0), or the pH coefficient is 0 in the pH range under consideration during the temperature change, the temperature change is determined from the following formula:

$$dT=\Delta\delta/C_T=(\delta_1-\delta_0)/C_T$$

where the measurement can be made either for $^1H$ or $^{31}P$. Both temperature and pH must be calculated for in vivo systems, because heating tissue can not only lead to changes in temperature but also changes in pH, particularly with lactic acid build-up. Accordingly, monitoring both factors is desirable for hyperthermia treatment of tumors.

In a preferred embodiment, the paramagnetic compound is a lanthanide complex, e.g., a lanthanide complex that has a temperature dependence of the $^1H$ chemical shift in the range of about 0.15 to about 2.00 ppm/°C., more preferably in the range of about 0.20 to about 1.00 ppm/°C. Similarly, the preferred compounds have a temperature dependence of the $^{31}P$ chemical shift in the range of about 0.01 to about 4.00 ppm/°C., more preferably in the range of about 1.00 to about 3.00 ppm/°C. In general, nuclei of the paramagnetic compound can be any two non-magnetic equivalent nuclear spins. The preferred compound for use in the invention is Thulium(III)-1,4,7,10-tetraazacyclododecane-1,4,7,10-tetrakis-(methylene phosphate) (TmDOTP$^{5-}$), which has a temperature dependence for $^1H$ of about 0.89 ppm/°C. and a temperature dependence for $^{31}P$ of about 2.18 ppm/°C. By comparing these results with other metal complexes such as Ytterbium or Praseodymium complexes, it appears that Thulium(III) lanthanide complexes are preferred, but other lanthanide complexes, e.g., Dysprosium, Cerium, Neodymium, Europium, Holmium, Samarium, Erbium, Terbium, Lutetium or Promethium lanthanide complexes are also within the scope of this invention. The preferred lanthanide metal ions are those which maximize the paramagnetic shift at the nucleus under observation, yet minimize paramagnetically induced line broadening since it may compromise the precision of the temperature measurement.

The present invention further pertains to methods for reducing tumor size or cancer in a subject. In general, these methods include the step of increasing the temperature of the tumor or cancerous tissue in said subject to a selected temperature such that a substantial number of cancer cells in said cancer tissue are killed. The present invention provides an improvement of the previous methods in that the temperature of the cancerous tissue can be measured by subjecting the cancer tissue to a magnetic field, e.g., using magnetic resonance, to measure change in cancer tissue temperature. The temperature measurement can stop over- or under-heating of the tissue, making sure that the tumor or cancerous tissue is eliminated while not harming healthy adjacent tissue. The method of the present invention can be carried out alone or in conjunction with other methods known in the art to treat tumors or cancers, e.g., chemotherapy or radiation therapy.

DETAILED DESCRIPTION OF THE INVENTION

The present invention pertains to methods for measuring temperature change in a biological tissue. These methods typically include the step of administering a paramagnetic compound, particularly a Thulium (III) lanthanide compound, to the biological tissue and subjecting the biological tissue to a magnetic field, possibly with varying strengths, e.g., using magnetic resonance apparatus. This type of in vivo, non-invasive temperature measurement has particular importance in hyperthemia treatment of tumors or other cancerous tissue, where accurate, localized temperature measurements are critical. However, the invention is not limited to use in cancerous or other biological tissue but rather, the method has general applicability.

The following definitions are useful in fully understanding the invention. The term "biological tissue" refers to a group of two or more cells of a living organism, such as a mammal. The term "paramagnetic compound" refers to compounds which exhibit magnetic properties in response to static, transient or induced magnetic fields but do not retain the magnetic properties in the absence of the magnetic field as do permanent or ferromagnetic materials. Examples of paramagnetic compounds include paramagnetic ions, chelated paramagnetic ions, and paramagnetic complexes, e.g., lanthanide complexes such as Thulium, Dysprosium, Cerium, Neodymium, Europium, Holmium, Samarium, Erbium, Terbium, Lutetium or Promethium lanthanide complexes.

The terms "cancer" and "cancer tissue" are used herein to refer to any type of neoplastic growth, benign or malignant. Examples of cancer which can be treated according to the method of the invention include solid tumors, e.g., solid tumors in organs such as the liver, the pancreas, the kidneys, and the lungs. The term "subject" is intended to include mammals, particularly humans, susceptible to neoplastic disease. "Selected temperatures" are temperatures at which particular cancer cells of interest are killed. For example, selected temperatures are typically temperatures 5°–20° C., preferably 5°–15° C., greater than normal mammalian body temperature (37° C.). Therefore, preferred selected temperatures generally range from about 43° C. to about 48° C.

Selected temperatures are typically attained by subjecting the tissue to microwave radiation, radio frequency currents, or high frequency sound waves.

The phrase "substantial number" refers to a number of tumor, e.g., cancerous, cells which are killed at the selected temperature. Death of a substantial number of cells preferably refers to death of at least about 50% or more of the tumor, e.g., cancerous, cells in the treated tissue.

In preferred embodiments, the paramagnetic compounds are the lanthanide complexes, particularly Thulium-based lanthanide complexes like TmDOTP. The paramagnetic compounds can be administered through any route which allows the compounds to perform their intended function. Examples of routes of administration which may be used in this method include parenteral, subcutaneous, intravenous, intramuscular, intra-arterial, intraperitoneal, intrathecal, intracardiac, intrasternal, enteral, mucosal, and percutaneous administration. The term "magnetic resonance," e.g., NMR imaging or spectroscopy, refers to a process in which selected nuclei are specially encoded and excited by suitable RF signals and magnetic field gradient signals transmitted into an object under thunder the influence of suitable magnetic fields.

Normaly, temperature and/or pH differences over time are measured but absolute values can also be calculated. If temperature measurements are made, the first and second temperature points at which the chemical shifts are measured according to the invention can be any selected temperature points.

The present invention further pertains to methods for treating cancer in a subject. In general, these methods include the steps of increasing cancer tissue temperature in said subject to a selected temperature such that a substantial number of cancer cells in said cancer tissue are killed. The present invention provides the improvement that temperature can be accurately measured non-invasively by subjecting said cancer tissue to a magnetic field, e.g., by magnetic resonance, to measure change in the temperature of the cancerous tissue. If there is no pH change with temperature, the following formula may be used:

$$\Delta T = (\sigma(T) - \sigma(T_0))/C_T$$

wherein $\sigma(T_0)$ is the measured chemical shift at a first temperature point and $\sigma(T)$ is the chemical shift at a second temperature point and $C_T$ is the temperature dependence of the chemical shift of the nuclear spin under measurement.

Lanthanide Complexes (TmDOTP$^{5-}$)

An ideal in vivo paramagnetic thermometric substance should have one or more, or preferably all of the following characteristics:

(i) have a chemical shift with a simple (e.g., linear) and sensitive temperature dependence over the temperature range of interest, (ii) be detected easily by virtue of a simple spectrum and high gyromagnetic ratio, (iii) be free of interfering background peaks in vivo, and (iv) have low toxicity in vivo (if it is a foreign material) so that high concentrations may be used.

The large chemical shift temperature dependence ($C_T$) of $^1$H and $^{31}$P in TmDOTP$^{5-}$ is a major advantage compared to many other substances currently used for NMR measurements of temperature in vivo. $C_T$ values of 0.89 ppm/°C. for $^1$H and 2.18 ppm/°C. for $^{31}$P yield nearly identical values of the frequency shift at 1.5 Tesla (~57 Hz/°C.), compared to $^2$0.7 Hz/°C. for $^1$H$_2$O and $^{19}$F in fluorocarbons (De Poorter et al., *J. Magn. Reson.* B103, 234–241 (1994); Shukla et al., *J. Magn. Reson.* B106, 131 (1995); Bornais and Brownstein, *J. Magn. Reson.* 29, 207–212 (1978)). This offers large potential improvements in the accuracy of temperature measurements under an induced magnetic field at clinically-relevant field strengths.

Figure 4A:
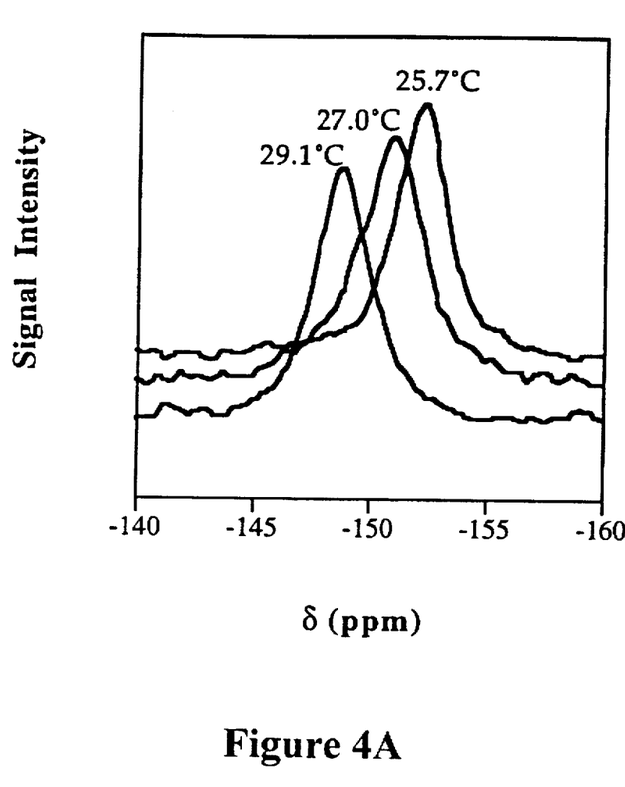
FIG. 4A depicts a portion of the in vivo spectrum of $^1H$ in TmDOTP$^{5-}$ at 25.7°, 27.0°, and 29.1° C. The chemical shift scale was established by assigning the water proton shift as 0 ppm. The spectrum was acquired with 1024 averages at $T_R$ of 30 ms and total acquisition time of 30s.

As a thermometric probe, TmDOTP$^{5-}$ possesses important advantages compared to $^{59}$Co complexes (Webbet al., "Proc., SMRM, 12th Annual Meeting, New York, 1993,"p. 245; Levy et al... *J. Magn. Reson.* 37, 353–356 (1980)). The higher gyromagnetic ratio of $^1$H makes it inherently more sensitive to NMR observation than $^{59}$Co. Furthermore, $^1$H spectra of lanthanide complexes can be observed using clinical magnetic resonance scanners without extended, broadband frequency capabilities. One potentially serious disadvantage of any foreign thermometric compound is that its in vivo concentration is necessarily low, at least compared to native substances such as $^1$H$_2$O. The properties of TmDOTP$^{5-}$ help overcome this problem in two ways. First, this complex appears to have low biological toxicity (Bansal et al., *J Magn. Reson. Imag.* 2, 385–391 (1992); Butwell et al., *Invest. Radiol.* 26, 1079–1082 (1991); Bansal et al., *Biochemistry* 32, 5638–5643 (1993)) so that relatively high dosages may be used. In addition, strong dipolar interactions between the paramagnetic center and the $^1$H and $^{31}$P nuclei in TmDOTP$^{5-}$ yield very short $T_1$s, enabling high spectral signal/noise to be achieved in a short time by rapid signal averaging. The repetition time $T_R$ (30 ms for in vivo studies) was controlled by the spectral width (10 kHz) instead of the $T_1$. With a dosage of 1 mmole TmDOTP$^{5-}$/kg, 1024 signal averages produced a proton spectrum with signal/noise of 65 in 0.5 minute (FIG. 4A). At the same dosage, 2048 averages acquired in 1 minute resulted in similar S/N for $^{31}$P as for $^1$H. Line fitting simulations indicated that a temperature resolution of 0.5° C. could be achieved using the spectrum of either nuclide. These results suggest that surface-coil localized spectroscopy of TmDOTP$^{5-}$ can provide NMR temperature measurements with acceptable thermal and temporal resolution for many in vivo applications such as hyperthermia.

The large chemical shifts of $^1$H (−140 ppm) and $^{31}$P (−320 ppm) in TmDOTP$^{5-}$ insure that spectra are essentially free of interfering background $^1$H and $^{31}$P peaks arising from the tissue itself. Any small residual IH signal due to the intense in vivo water line can be avoided by using a gaussian RF pulse centered at the $^1$H resonance frequency of TmDOTP$^{5-}$. The temperature dependence of the chemical shift is regulated by the distance between the observed nuclide and the nearby unpaired electron in the complex, and the temperature coefficient of the lanthanide element (Abragam, "*Principles of Nuclear Magnetism*," Oxford University Press, Oxford, 1961; Bloembergen and Morgan, *J. Chem. Phys.* 34, 841 (1961); Dragoet al., *J. Chem. Educ.* 51, 371–376, 464–467 (1974); Dwek, "*NMR in Biochemistry*," Clarendon Press, Oxford, 1973). Therefore, diamagnetic shift effects due to physiologically-relevant pH changes in the surrounding medium are minimal (Dwek, "*NMR in Biochemistry*," Clarendon Press, Oxford, 1973). Since the temperature is calculated from the chemical shift difference between the $^1$H peaks or $^{31}$P peaks of TmDOTP$^{5-}$ and the $^1$H$_2$O or phosphocreatine signals of the tissue, changes in bulk susceptibility or local magnetic field strength have little effect on the accuracy of the measurement. Although suitable calibration permits TmDOTP$^{5-}$ to be used for absolute temperature measurements, most applications are likely to involve only the determination of changes in temperature. In such cases, only the relative variations in TmDOTP$^{5-}$ chemical shift are of interest, and the shifts of in vivo water or phosphocreatine (PCr) need not be measured provided bulk susceptibility changes are negligible.

Compared to other paramagnetic lanthanide complexes recently reported, the temperature dependencies of the chemical shifts for both $^{31}$P and $^1$H in TmDOTP$^{5-}$ (2.2 and 0.89 ppm/°C., respectively) were considerably higher than those reported for $^1$H in Pr-MOE-DO3A (0.13 ppm/°C.) or a $^1$H methyl resonance in YbDOTMA (0.04ppm/°C.) (Aime et al., *Magn. Reson. Med.* 35, 648–651 (1996); Frenzel et al., *Magn. Reson. Med.* 35, 364–369 (1996)). The paramagnetic shifts of lanthanide complexes are known to be inversely proportional to temperature (Bleaney, *J. Magn. Reson.* 8, 91–100 (1972); Dwek, "*NMR in Biochemistry*," Clarendon Press, Oxford, 1973). The proportionality constant between the measured shift and the temperature depends upon the identity of the lanthanide cation and the geometry of the complex (Bryden and Reilley, *Anal Chem.* 53, 1418–1425 (1981); Alsaadiet al., *J. C. S. Dalton* 271, 2151–2154 (1980)). Previous studies on lanthanide complexes suggest that the metal cation TM$^{+3}$ may play an important role in the higher temperature dependence of the $^1$H chemical shift in TmDOTP$^{5-}$ (Bryden and Reilley, *Anal. Chem.* 53, 1418–1425 (1981); Alsaadiet al., *J. C. S. Dalton* 271, 2151–2154 (1980)). In principle, those nuclei showing the largest paramagnetic shifts should also be most sensitive to changes in temperature. Using the data available for four nuclei ($^1$H and $^{31}$p in TmDOTP$^{5-}$, $^1$H in Pr-MOE-DO3A, and $^1$H in YbDOTMA), a linear relationship between the magnitude of the paramagnetic shift (in ppm) and the temperature dependence (in ppm/°C.) is found ($r^2=0.999$). The design of new lanthanide thermometric complexes for monitoring temperature in vivo should maximize the paramagnetic shift at the nucleus under observation, yet minimize paramagnetically induced line broadening since it may compromise the precision of the temperature measurement. Ultimately, proper combinations of ligands and paramagnetic metal cations could optimize the temperature dependence of the chemical shift, the relaxation properties, and the toxicity.

Finally, TmDOTP$^{5-}$ was found to be stable up to ~90° C. and was used for temperature measurements from ~4° C. to ~50° C. in the experiments described below. Nevertheless, if the temperature is too high, the molecule could decompose and this precludes its use in high temperature applications such as laser surgery. Fortunately, high temperatures have profound effects on the content and relaxation properties of tissue water which may be used for temperature measurements, so there is little need to use TmDOTP$^{5-}$ in these applications.

This invention is further illustrated by the following Example which should not be construed as limiting. The contents of all references and published patents and patent applications cited throughout the application are hereby incorporated by reference.

EXEMPLIFICATION

Example

Figure 1:
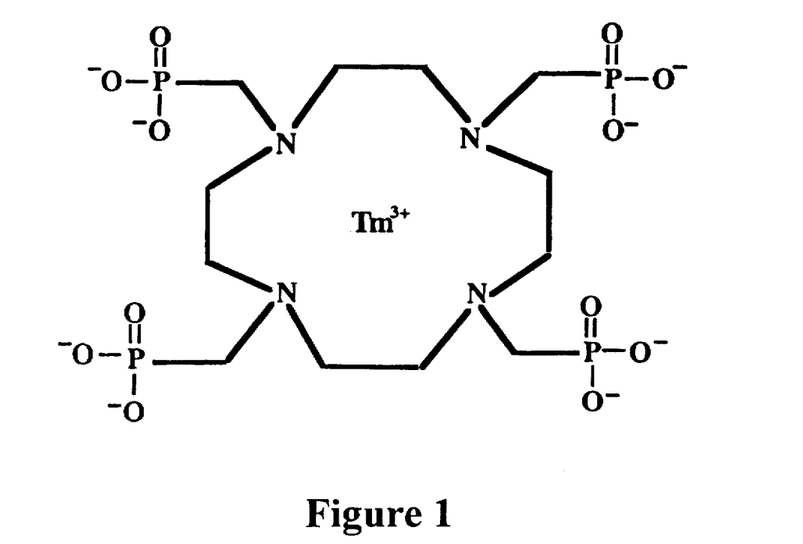
FIG. 1 is a schematic diagram depicting the molecular structure of Thulium(III)-1,4,7,10-tetraazacyclododecane-1,4,7,10-tetrakis-(methylene phosphate) (TmDOTP$^{5-}$).

The methods and materials used in this Example were as follows:
Materials and Methods TmDOTP$^{5-}$ (FIG. 1) was prepared as described previously (Bansal et al., *J. Magn. Reson. Imag.* 2, 385–391 (1992); Buster et al., *Magn. Reson. Med.* 15, 25–32 (1990)). Some solutions were made in deuterium oxide (99.9%, Cambridge Isotopes, Woburn, Mass., USA) to facilitate the detection of the protons in TmDOTP$^{5-}$. Experiments were performed using TmDOTP$^{5-}$ concentrations of 5 mM, 20 mM, and 40 mM. Similar results were obtained across this concentration range. The in vitro results in this study were from experiments performed with 20 mM TmDOTP$^{5-}$ solutions.

Measurements of the temperature dependence of the $^{31}$P and $^1$H chemical shifts were performed using a 7.06 Tesla General Electric GN-300WB spectrometer with a 10 mm probe and GE variable temperature controller. Spectra were acquired using a one-pulse sequence, and $T_1$'s of $^1$H and $^{31}$P in TmDOTP$^{5-}$ were estimated using the inversion recovery technique. Line widths at 7.06 Tesla were determined using a magnetic field homogeneity better than ±0.002 ppm, as measured from the width of an internal sodium 3-(trimethylsilyl)propionate-2,2,3,3-d$_4$ (TSP) line.

In vivo measurements were performed using a 4.7 Tesla Bruker Biospec imaging/spectroscopy system equipped with surface coils resonating at $^1$H and $^{31}$P frequencies. Five rats weighing approximately 300 g were studied. The blood vessels to the kidneys of each rat were ligated under pentobarbital anesthesia to prevent clearance of TmDOTP$^{5-}$. 75 mM TmDOTP$^{5-}$ in saline was injected intraperitoneally to produce a total dosage of 1 mmole/kg. A 2.5 cm diameter surface coil was used to acquire NMR signals in the abdominal region, and a copper-constantan thermocouple was placed beneath the muscle of the abdomen to monitor the temperature. Following the anesthetization and surgery, the temperature of the abdominal region fell and finally stabilized at about 29° C. in the magnetic field. The thermocouple was disconnected during NMR data acquisition to prevent extra noise from being introduced into the spectrum. The temperature for each NMR measurement was estimated from the mean of thermocouple readings obtained immediately before and after spectral data collection. To alter the temperature, a bag containing ice or warm water was placed externally in contact with the abdomen in the region of the surface coil. $^1$H spectra were acquired using a 1 ms gaussian RF pulse to selectively excite the TmDOTP$^{5-}$ signal without interference from the $^1$H$_2$O resonance line. The RF power was adjusted to optimize signal/noise for TmDOTP$^{5-}$. Other $^1$H acquisition parameters included a 10 kHz spectral width, 30 ms $T_R$, averaging 1024 values, and a total data collection time of 0.5 min. $^{31}$P spectra were acquired using 50 μs rectangular RF pulses, a 10 kHz spectral width, 30 ms $T_R$, 2048 averages, and a total data collection time of 1 min. The spectra were processed on a Macintosh Quadra 700 with the software package MacFID (Techmag, Houston, Tex., USA). All chemical shifts and signal/noise values in the frequency domain were measured after matched filtering by exponential weighting in the time domain. For experimental convenience, water and phosphocreatine (PCr) signals were used as references for in vivo $^1$H and $^{31}$P chemical shifts, respectively. The choice of reference does not affect the slope ($C_T$) of the TmDOTP$^{5-}$ shift vs. temperature curve but does change the intercept ($C_D$).

Figure 2:
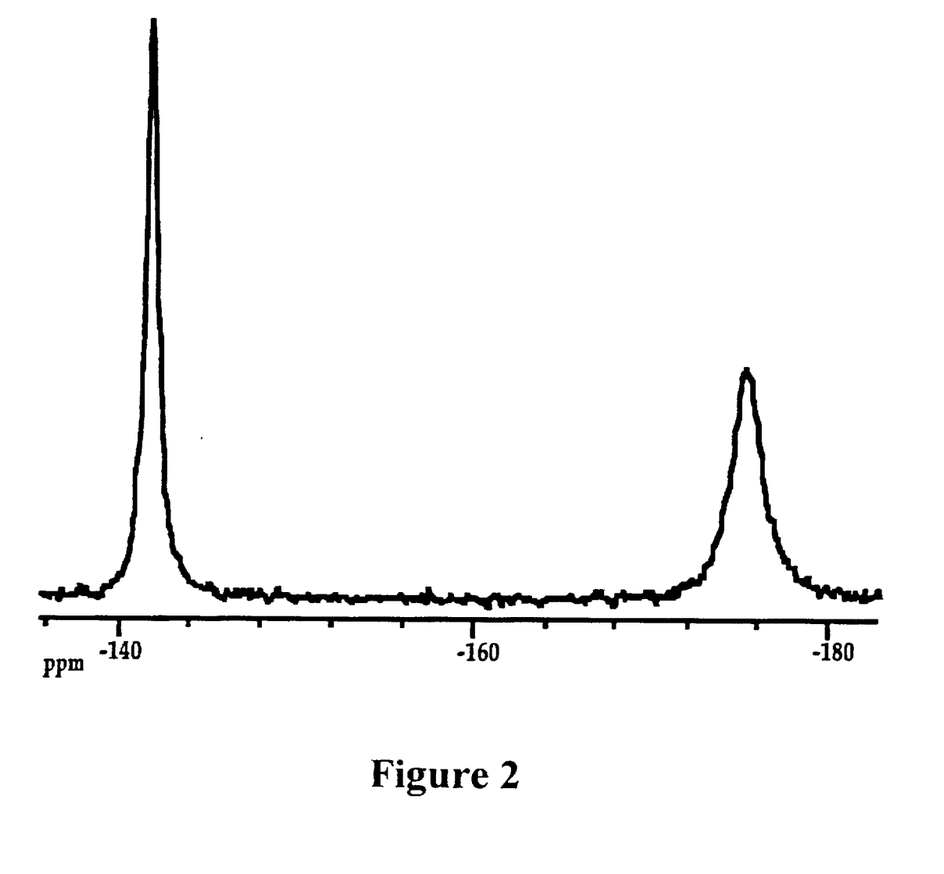
FIG. 2 depicts a portion of the $^1H$ NMR spectrum of 20 mM TmDOTP$^{5-}$-D$_2$O solution. The spectrum was acquired in 2.4 s at 7.06 Tesla, 37° C. and pH ~6.3 using 100 averages and a repetition time of 24 ms.

The temperature and pH dependencies of $^1$H and $^{31}$P ($C_{T^H},C_{T^P},C_{pH^H},C_{PH^P}$) were calculated from adjacent data points.
Results 1) Phantom Studies Due to the inherent four fold symmetry, each TmDOTP$^{5-}$ molecule (FIG. 1) contains four magnetically equivalent phosphorus nuclei and six magnetically non-equivalent groups of protons, with three paramagnetically shifted upfield and three paramagnetically shifted downfield (Geraldes et al., *J. Magn. Reson.* 97, 290–304 (1992)). A portion of the proton spectrum of TmDOTP$^{5-}$ acquired at 37° C. and 7.06 Tesla is shown in FIG. 2. This part of the spectrum contained two peaks that have been previously assigned to H$_1$ and H$_6$ (Geraldes et al., *J. Magn. Reson.* 97, 290–304 (1992)). H$_1$, one of the ethylene protons of the macrocyclic ring (Geraldes et al., *J. Magn. Reson.* 97, 290–304 (1992)), was about 176 ppm upfield from TSP at 37° C. with a line width of about 3 ppm. H$_6$, one of the side chain methylene protons, was about 142 ppm upfield from TSP at 37° C. with a line width of approximately 1 ppm (Geraldes et al., *J. Magn. Reson.* 97, 290–304 (1992)). The ratio of the areas under the resonances was H$_1$: H$_6$=1.01:1.00. Since the line width of H$_6$ was much smaller than that of H$_1$, subsequent measurements focused only on H$_6$. Hence, $^1$H in TmDOTP$^{5-}$ refers to H$_6$ in all discussions below. The $^{31}$P peak of TmDOTP$^{5-}$ had a width of about 1 ppm and, at 37° C., was approximately 324 ppm upfield from the signal of 85% phosphoric acid contained in a microsphere inserted into the sample.

Figure 3A:
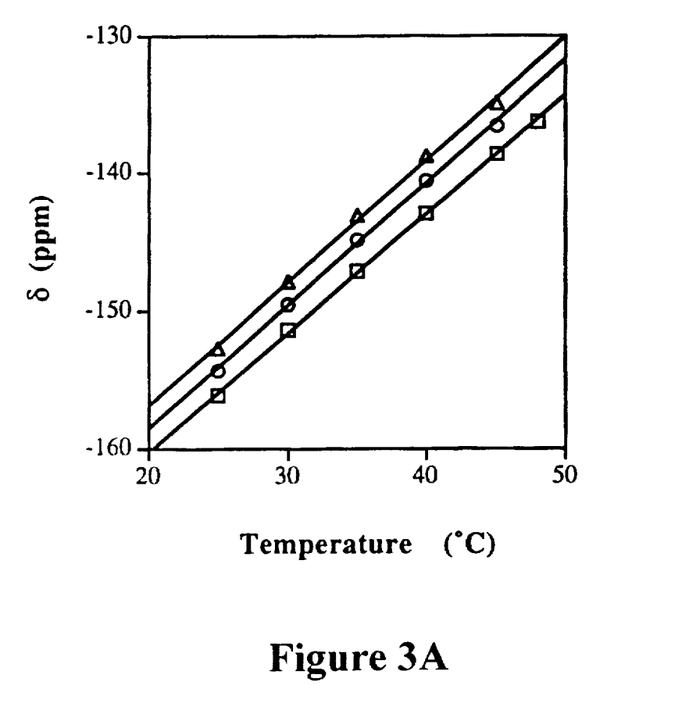
FIG. 3A is a graph showing the temperature dependence of the $^1H$ chemical shift in TmDOTP$^{5-}$ at several pH values. The slope was 0.89±0.03 ppm/°C. in all cases. Triangles indicate pH 6.8, circles indicate pH 7.2, and squares indicate pH 8.2.
Figure 3B:
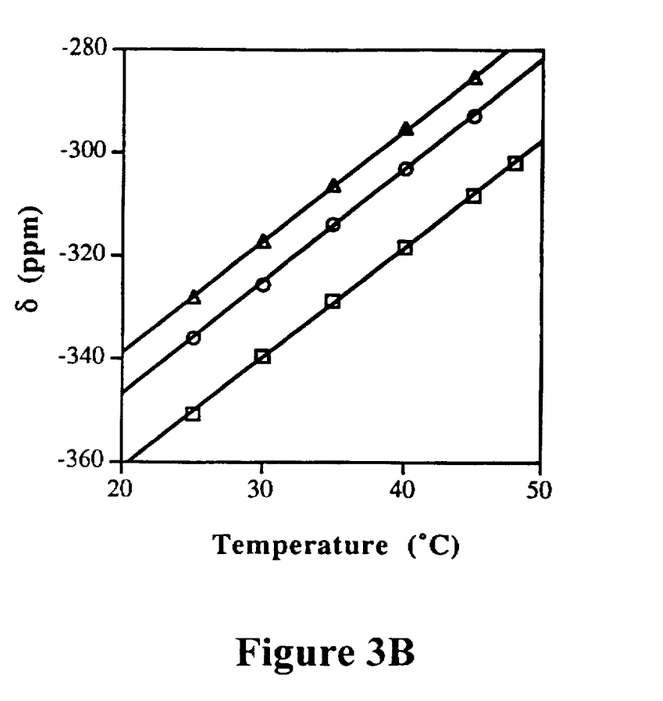
FIG. 3B is a graph showing the temperature dependence of the $^{31}P$ chemical shift in TmDOTP$^{5-}$ at several pH values. The slope was 2.18±0.03 ppm/°C. in all cases. Triangles indicate pH 6.8, circles indicate pH 7.2, and squares indicate pH 8.2.

The temperature dependence of the $^1$H chemical shift in TmDOTP$^{5-}$ was found to be a constant, 0.89±0.03 ppm/°C. ($r^2$=0.995), for pH 6.5–8.5 over the temperature range from 25° to 47° C. (FIG. 3A). The $^{31}$P chemical shift over the same temperature range also showed a linear dependence ($r^2$=0.999) with a slope of 2.18±0.02 ppm/°C. (FIG. 3B). As shown in FIGS. 3A and 3B, the chemical shift temperature dependencies of $^1$H and $^{31}$P in TmDOTP$^{5-}$ (i.e., the slopes of the lines) were independent of pH between pH 6 and 8 although the absolute values of the chemical shifts were not. The chemical shifts of both $^1$H and $^{31}$P were independent of TmDOTP$^{5-}$ concentration in the 5–40 mM range, as expected for a stable as opposed to a transient complex. $^1$H and $^{31}$P in TmDOTP$^{5-}$ were found to relax very rapidly at 37° C. and 7.06 T (T$_1{}^H$=2 ms and T$_1{}^P$=3 ms).

Figure 4B:
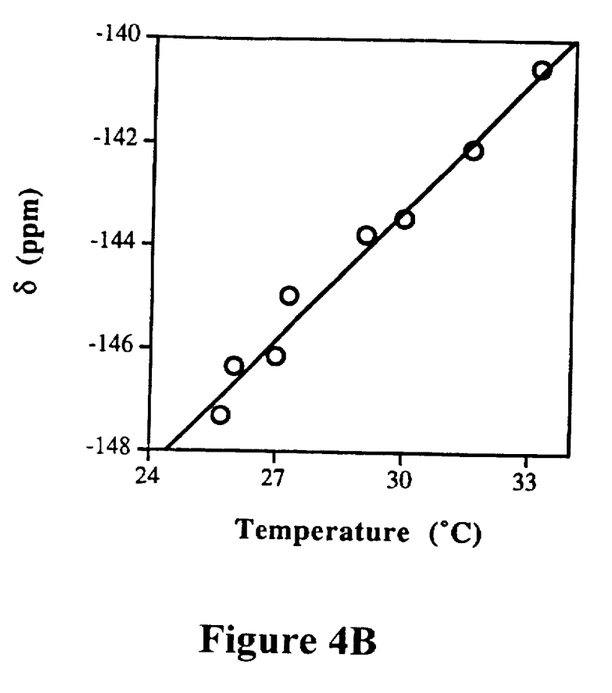
FIG. 4B is a graph showing in vivo measurements of the TmDOTP$^{5-}$-$^1H$ chemical shift versus temperature. The chemical shift was referenced to in vivo $^1H_2O$ at δ=0 ppm. The temperature dependence of the chemical shift was 0.83 ppm/°C.
Figure 5:
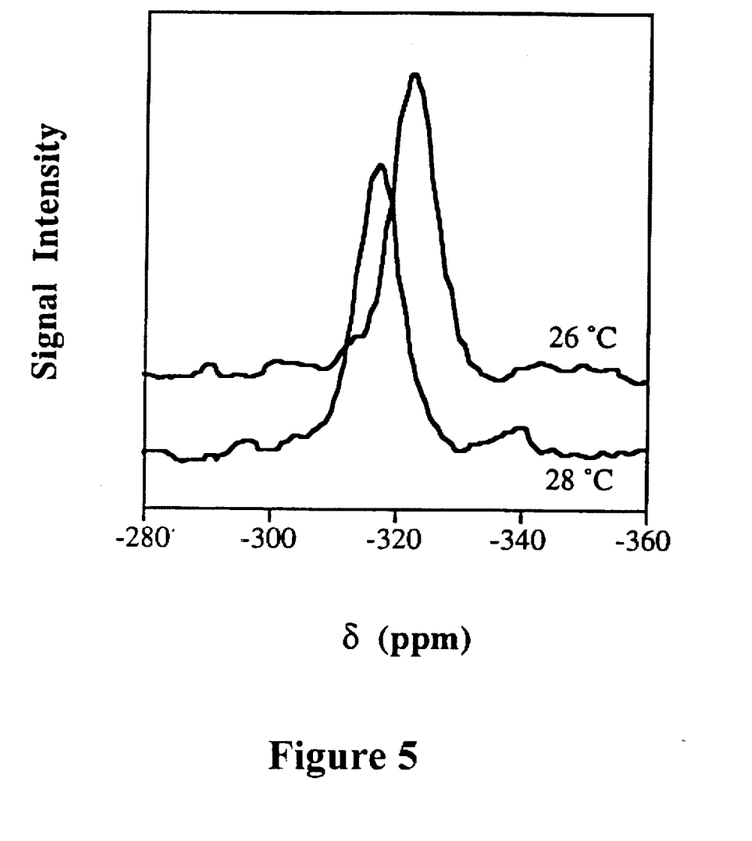
FIG. 5 depicts in vivo NMR spectra of $^{31}P$ in TmDOTP$^{5-}$ at 26° and 28° C. The chemical shift was referenced to in vivo phosphocreatine (PCr) at δ=0 ppm. The spectra were acquired with 2048 averages at $T_R$ of 30 ms and total acquisition time of 1 min.

2) In vivo Studies $^1$H and $^{31}$P chemical shifts were measured in vivo over temperatures ranging from 25° to 32° C. FIG. 4A shows three spectra of $^1$H in TmDOTP$^{5-}$ acquired at temperatures of 25.7° C., 27.0° C. and 29.1° C. The width of the line was about 2.7 ppm, and the signal to noise ratio (S/N) was about 65. The resonance frequency difference between 25.7° C. and 29.1° C. was about 3.6 ppm. The temperature dependence of the $^1$H chemical shift was found to equal the measured in vitro value within experimental error (FIG. 4B) in the temperature range of 25° to 32° C. The $^{31}$P line width in vivo was about 4 ppm, and signal averaging for 1 min was found to produce a $^{31}$P S/N of about 61. FIG. 5 shows spectra of $^{31}$P in TmDOTP$^{5-}$ at 26° and 28° C., where the chemical shift was referenced to PCr at 0 ppm. The $^{31}$P signal shifted by about 4.5 ppm between 26° and 28° C.

The chemical shifts of $^1$H and $^{31}$P in TmDOTP$^{5-}$ are two orders of magnitude more sensitive to temperature than are the shifts of water proton and $^{19}$F in fluorocarbons and at least 7 times more sensitive than other lanthanide complexes recently reported for use as thermometric substances. In the physiological relevant pH range of 6–8 and over a temperature range of 20°–50° C., the chemical shift of $^1$H and $^{31}$P in TmDOTP has a linear relationship with temperature and pH, and the temperature dependence of the chemical shift can be separated from its pH dependence. Efficient spin relaxation allows rapid signal averaging to compensate for low in vivo concentrations. The large chemical shifts of $^1$H and $^{31}$P in TmDOTP$^{5-}$ provide spectra free of background signals from existing in vivo protons and phosphorus. NMR spectroscopy of the lanthanide complex TmDOTP$^{5-}$ is a potentially useful approach for measurements of temperature in vivo at clinical magnetic field strengths. Utilizing paramagnetic thermometric substances, e.g., lanthanide complexes, therefore, impacts magnetic resonance measurements of temperature and pH.

Other embodiments are within the following claims.

What is claimed is:

1. A method for measuring temperature change in a biological tissue, said method comprising:

(a) administering a lanthanide paramagnetic complex to said biological tissue;

(b) subjecting said biological tissue to a magnetic field;

(c) measuring the chemical shift caused by said magnetic field; and (d) calculating the temperature of said biological tissue from said chemical shift.

wherein said lanthanide paramagnetic complex has a temperature dependence of the $^1$H chemical shift in the range of about 0.15 to about 2.00 ppm/°C. or said lanthanide paramagnetic complex has a temperature dependence of the $^{31}$P chemical shift in the range of about 0.01 to about 4.00 ppm/°C.

2. The method of claim 1 wherein said lanthanide paramagnetic complex comprises a Thulium lanthanide complex.

3. The method of claim 2 wherein said Thulium lanthanide complex is Thulium(III)-1, 4,7,10-tetraazacyclododecane-1,4,7,10-tetrakis-(methylene phosphate).

4. A methods for reducing cancerous tissue in a subject, said method comprising increasing the temperature in said cancerous tissue in said subject to a selected temperature such that a substantial number of the cancer cells in said cancerous tissue are killed while monitoring the temperature of said cancerous tissue non-invasively to make sure that said selected temperature is maintained in said cancerous tissue, said non-invasive monitoring being carried out by the steps of:

(a) administering a paramagnetic compound to said cancerous tissue;

(b) subjecting said cancerous tissue to a magnetic field;

(c) measuring the chemical shift caused by said magnetic field; and (d) calculating the temperature of said cancerous tissue from said chemical shift.

5. The method of claim 4 wherein said paramagnetic compound has a temperature dependence of the $^1$H chemical shift in the range of about 0.15 to about 2.00 ppm/°C.

6. The method of claim 4 wherein said paramagnetic compound has a temperature dependence of the $^{31}$P chemical shift in the range of about 0.01 to about 4.00 ppm/°C.

7. The method of claim 4 wherein said paramagnetic compound comprises a lanthanide complex.

8. The method of claim 7 wherein said lanthanide complex is selected from the group consisting of Thulium lanthanide complexes, Cerium lanthanide complexes, Neodymium lanthanide complexes, Europium lanthanide complexes, Holmium lanthanide complexes, Dysprosium lanthanide complexes, Samarium lanthanide complexes, Erbium lanthanide complexes, Terbium lanthanide complexes, Lutetium lanthanide complexes or Promethium lanthanide complexes.

9. The method of claim 8 wherein said Thulium lanthanide complex is Thulium(III)-1, 4,7,10-tetraazacyclododecane-1,4,7,10-tetrakis-(methylene phosphate).

* * * * *